United States Patent
Katori et al.

(10) Patent No.: US 11,442,062 B2
(45) Date of Patent: Sep. 13, 2022

(54) POLY(ETHYLENE GLYCOL) DERIVATIVE AND PROTEIN-ADSORPTION INHIBITOR

(71) Applicant: NOF Corporation, Tokyo (JP)

(72) Inventors: Akane Katori, Kanagawa (JP); Masaru Matsuda, Kanagawa (JP); Tomozumi Noda, Kanagawa (JP); Takashi Sasaki, Kanagawa (JP); Hirotaka Suzuki, Kanagawa (JP); Nobuyuki Sakamoto, Kanagawa (JP)

(73) Assignee: NOF Corporation, Tokyo (JP)

( * ) Notice: Subject to any disclaimer, the term of this patent is extended or adjusted under 35 U.S.C. 154(b) by 401 days.

(21) Appl. No.: 16/645,862

(22) PCT Filed: Aug. 28, 2018

(86) PCT No.: PCT/JP2018/031801
§ 371 (c)(1),
(2) Date: Mar. 10, 2020

(87) PCT Pub. No.: WO2019/049734
PCT Pub. Date: Mar. 14, 2019

(65) Prior Publication Data
US 2020/0271642 A1    Aug. 27, 2020

(30) Foreign Application Priority Data
Sep. 11, 2017  (JP) .............................. JP2017-173725

(51) Int. Cl.
*G01N 33/53*  (2006.01)
*C08G 65/335* (2006.01)
*G01N 33/531* (2006.01)

(52) U.S. Cl.
CPC ....... *G01N 33/531* (2013.01); *C08G 65/3358* (2013.01); *G01N 33/5306* (2013.01)

(58) Field of Classification Search
CPC ............. G01N 33/531; G01N 33/5306; G01N 33/54393; C08G 65/3358; C08G 65/3356; C08G 65/327; C08G 65/325
See application file for complete search history.

(56) References Cited

FOREIGN PATENT DOCUMENTS

| CN | 102070780 A | 5/2011 |
|---|---|---|
| CN | 103282368 A | 9/2013 |
| CN | 106589290 A | 4/2017 |
| CN | 106749477 A | 5/2017 |
| EP | 2669287 A1 | 12/2013 |
| JP | H07-083923 A | 3/1995 |
| JP | 2015-117269 A | 6/2015 |
| WO | 2012-086762 A1 | 6/2012 |

OTHER PUBLICATIONS

Chinese Office Action dated Jan. 24, 2022 issued in Chinese Patent Application No. 201880058415.0.
International Search Report and Written Opinion dated Oct. 9, 2018 from International Application No. PCT/JP2018/031801, with partial translation.
Supplementary European Search Report dated Mar. 19, 2021 from European Patent Application No. 18854320.1.
Tanaka et al., "Synthesis of Phosphorylcholine-Oligoethylene Glycol-Alkane Thiols and Their Suppressive Effect on Non-Specific Adsorption of Proteins," Tetrahedron Letters, vol. 50, May 3, 2009, pp. 4092-4095.

*Primary Examiner* — Tracy Vivlemore
*Assistant Examiner* — Nam P Nguyen
(74) *Attorney, Agent, or Firm* — Amster, Rothstein & Ebenstein LLP

(57) ABSTRACT

A compound is provided which is effectively adsorbed to a substrate surface, such as an immune reaction vessel, has extremely high protein adsorption inhibitory effect that inhibits non-specific adsorption of protein or the like, and has excellent washability to retain the inhibitory effect before and after washing operation of the substrate. Also provided are a protein adsorption inhibitor using the compound, a phosphorylcholine-modified substrate, and a method for inhibiting protein adsorption. The compound is a phosphorylcholine group-containing polyethylene glycol derivative represented by formula (1). The method for inhibiting protein adsorption of the present invention includes the step of forming an adsorbed layer of the derivative on a substrate surface.

$$H_2N\text{---}(CH_2)_m\text{---}O\text{---}(CH_2CH_2)_n\text{---}S\text{---}CH_2\text{---}CH(CH_3)\text{---}C(=O)\text{---}O\text{---}CH_2CH_2\text{---}O\text{---}P(=O)(O^-)\text{---}O\text{---}CH_2CH_2\text{---}N^+(CH_3)_3 \quad (1)$$

5 Claims, No Drawings

POLY(ETHYLENE GLYCOL) DERIVATIVE AND PROTEIN-ADSORPTION INHIBITOR

CROSS-REFERENCE TO RELATED APPLICATIONS

This application is a U.S. national stage entry under 35 U.S.C. § 371 of PCT International Patent Application No. PCT/JP2018/031801, filed Aug. 28, 2018, which claims priority to Japanese Patent Application No. 2017-173725, filed Sep. 11, 2017, the contents of each of which are hereby incorporated by reference in their entirety.

FIELD OF ART

The present invention relates to a novel compound that may be applied to surface treatment of a natural or synthesized material (substrate) or a surface treatment of protein, in particular to a novel compound that is applicable to a surface treatment agent for inhibiting non-specific adsorption of protein to a substrate or the like (protein adsorption inhibitor). The present invention also relates to a surface-modified material in which the compound is used as a protein adsorption inhibitor.

More specifically, the present invention relates to a novel phosphorylcholine group-containing polyethylene glycol derivative which inhibits non-specific adsorption of protein in a labeled antibody or antigen or a specimen in a measurement using immune response, to the surface of a substrate used, as well as a phosphorylcholine-modified substrate, surface-coated with the derivative. The present invention further relates to a method for inhibiting protein adsorption to a substrate wherein the derivative is used as a protein adsorption inhibitor.

BACKGROUND ART

There have widely been proposed surface treatment agents that can impart biocompatibility, antithrombogenicity, or surface hydrophilicity or the like derived from phosphorylcholine groups by treating various material surfaces with a compound having a phosphorylcholine group. Such agents may be used for protein surface treatment for protein hydrophylization, antifouling treatment of industrial filter surfaces, or surface treatment for inhibiting adsorption of protein or blood cells to medical polymer materials. Recently, in particular, protein adsorption inhibitors containing a phosphorylcholine group-containing compound as its component are used in measurement systems using immune response in the fields of clinical tests and diagnostic pharmaceuticals. It is known that addition of a protein adsorption inhibitor containing a phosphorylcholine group-containing compound is important in the methods for detecting a slight amount of biogenic substances, for the purpose of inhibiting non-specific adsorption of an antibody or antigen to be determined, to substrate surfaces, such as immune reaction vessels.

Patent Publication 1 discloses the effect of 2-methacryloyloxyethyl phosphorylcholine polymer to inhibit protein adsorption to a substrate surface. The invention disclosed in Patent Publication 1 is characterized by the use of the polymer, which has a strong protein adsorption inhibiting property, to enable analysis of a target substance at a high degree of accuracy in analyses of various bio-related substances.

Patent Publications 2 and 3 disclose an amino group-containing phosphorylcholine compound and a novel polymer that are capable of binding by chemical reaction to a substrate surface. The invention disclosed in Patent Publication 2 is characterized by the highly reactive amino group in the compound of the invention, which enables modification of a substrate surface with the compound to impart the functions of the compound to the substrate. The invention disclosed in Patent Publication 3 is characterized by firm binding of the novel polymer to a substrate surface, which provides high blocking effect for inhibiting non-specific adsorption to allow determination of a slight amount of a biogenic substance at sufficient sensitivity.

PRIOR ART PUBLICATION

Patent Publication 1: JP-H07-083923-A
Patent Publication 2: WO 2012/086762
Patent Publication 3: JP-2015-117269-A

SUMMARY OF THE INVENTION

Problem to be Solved by the Invention

The method of Patent Publication 1, however, has a problem that 2-methacryloyloxyethyl phosphorylcholine polymer may be desorbed from the substrate through a plurality of washing, resulting in possible deterioration of the protein adsorption inhibitory effect after the washing. The compound of Patent Publication 2 has a problem that bonding of an amino group and a phosphorylcholine group via an ethyl group results in insufficient protein adsorption inhibitory effect. The compound of Patent Publication 3, which is a polymer, has a problem of a high molecular weight and steric repulsion against antibodies or antigens, which discourage the binding ratio of a protein adsorption inhibitor and may result in insufficient protein adsorption inhibitory effect. In particular, it was difficult in the prior art to inhibit protein adsorption to magnetic microparticles, which are intended to highly sensitive measurements.

It is therefore an object of the present invention to provide a compound which is effectively adsorbed to a substrate surface, such as an immune reaction vessel, has extremely high protein adsorption inhibitory effect that inhibits non-specific adsorption of protein or the like, and has excellent washability to retain such effect before and after the washing operation of the substrate, as well as a protein adsorption inhibitor using the compound.

It is another object of the present invention to provide a phosphorylcholine-modified substrate wherein the compound is adsorbed on a substrate surface.

It is a further object of the present invention to provide an effective method for inhibiting protein adsorption to a substrate by means of the compound.

Means for Solving the Problem

The present inventors have made intensive researches in view of these problems, to find out that a polyethylene glycol derivative having an amino group and a phosphorylcholine group at respective terminals has a high adsorption property to a substrate surface, such as immune reaction vessels, and excellent washability, to thereby complete the present invention.

According to the present invention, there is provided a phosphorylcholine group-containing polyethylene glycol derivative represented by formula (1):

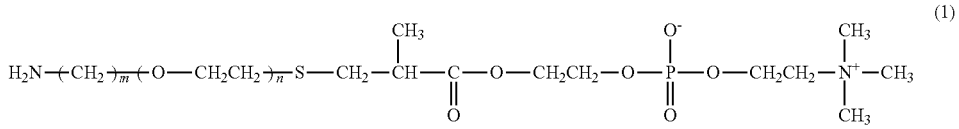

wherein m is an integer of 1 to 10, and n is an integer of 20 to 200.

According to another aspect of the present invention, there is provided a protein adsorption inhibitor comprising the above-mentioned phosphorylcholine group-containing polyethylene glycol derivative as an active component.

According to another aspect of the present invention, there is provided a protein adsorption inhibitor solution comprising 0.01 to 20 mass % of the above-mentioned phosphorylcholine group-containing polyethylene glycol derivative.

According to still another aspect of the present invention, there is provided a phosphorylcholine-modified substrate consisting of a substrate and the above-mentioned phosphorylcholine group-containing polyethylene glycol derivative, wherein the derivative is adsorbed to a substrate surface.

According to a further aspect of the present invention, there is provided a method for inhibiting protein adsorption to a substrate, comprising forming an adsorbed layer of the above-mentioned phosphorylcholine group-containing polyethylene glycol derivative by treating a substrate surface with the above-mentioned protein adsorption inhibitor solution.

Effect of the Invention

The phosphorylcholine group-containing polyethylene glycol derivative according to the present invention may profoundly inhibit non-specific adsorption of protein to a substrate surface by being effectively adsorbed to a substrate surface, such as an immune reaction vessel. That is, the derivative exhibits a high protein adsorption inhibitory property. The derivative also has a strong adsorbability to a substrate and thus high washability, and is hardly desorbed from the substrate through washing. In other words, the derivative has an extremely high washability, so that the protein adsorption inhibitory property may highly be maintained even through repeated washing after every measurement.

By treating a substrate surface with the protein adsorption inhibitor solution of the present invention, the phosphorylcholine group-containing polyethylene glycol derivative of the present invention may firmly be adsorbed to a substrate surface.

The phosphorylcholine-modified substrate according to the present invention, which is obtained by having the phosphorylcholine group-containing polyethylene glycol derivative adsorbed on a substrate surface, has high protein adsorption inhibitory property and excellent washability, so that the protein adsorption inhibitory property may be maintained at a high level.

The method for inhibiting protein adsorption to a substrate surface of the present invention, which allows firm adsorption of the phosphorylcholine group-containing polyethylene glycol derivative to a substrate surface, may profoundly inhibit non-specific adsorption of protein.

EMBODIMENTS OF THE INVENTION

The phosphorylcholine group-containing polyethylene glycol derivative according to the present invention is represented by formula (1) below. The compound represented by formula (1) may sometimes be referred to simply as the present derivative hereinbelow. The present derivative has a polyethylene glycol portion and a phosphorylcholine group portion in a molecule, and is capable of being firmly adsorbed to a surface of various substrates, such as immune reaction vessels and measuring instrument.

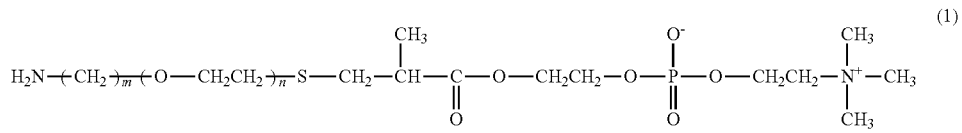

In formula (1), m is an integer of 1 to 10, preferably 2 to 5. Represented by n is the number of units —O—CH$_2$CH$_2$— calculated from the molecular weight or the like of formula (1), and is an integer of 20 to 200. The value of n is preferably 20 to 100, more preferably 20 to 50, and particularly preferably 40 to 50. With n and m within these ranges, effective adsorption to a surface of a substrate, such as immune reaction vessels, is achieved to profoundly inhibit non-specific adsorption of protein. The compound represented by formula (1) is in the state of a mixture of two or more compounds having different values of m or n or the like, and may be used in a protein adsorption inhibitor or a protein adsorption inhibitor solution to be discussed later.

The present derivative may have an amine salt structure. That is, the amine at the polyethylene glycol side terminal may form various salts with various acids. Such salts may be, for example, hydrochloride, acetate, sulfate, trifluoroacetate, bromate, or methanesulfonate.

Next, an embodiment of the method for preparing the present derivative will be discussed. The present derivative may be prepared by reacting a compound represented by formula (2) (α-aminoalkyl-ω-mercaptoethoxy-polyoxyethylene) or an amine salt thereof and 2-(methacryloyloxy)ethyl-2-(trimethylammonio)ethyl phosphoate represented by formula (3) (sometimes referred to as MPC hereinbelow) in, for example, an alcohol solvent in the presence of an amine catalyst, such as diisopropylamine. Hereinbelow, reference to the compound represented by formula (2) also include amine salts thereof. Acids forming the salts may be those listed above as the acids forming the amine salts of the present derivative.

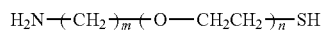

(2)

In formula (2), m is an integer of 1 to 10, and n is an integer of 20 to 200.

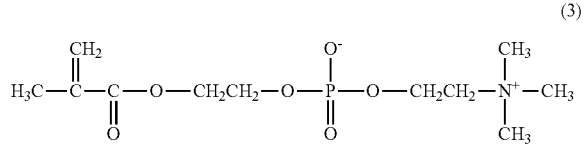

(3)

In the reaction of the compound of formula (2) and the compound of formula (3), the reaction ratio is preferably 0.6 to 1.5 mole of the compound of formula (2) with respect to 1 mole of the compound of formula (3). At less than 0.6 mole, production yield of the present derivative may be low. At over 1.5 mole, side reactions may occur, such as decomposition reaction of MPC of the formula (3), or Michael addition reaction of the amino group of the compound of formula (2) to the double bond, and the production yield of the present derivative may also be low.

The solvent used in the preparation of the present derivative is not particularly limited as long as the solvent dissolves and does not react with the compounds of formulae (2) and (3). Specifically, in addition to the alcohol solvents mentioned above, ketone solvents, ester solvents, ether solvents, and nitrogen-containing solvents may be used. The alcohol solvents may be methanol, ethanol, n-propanol, 2-propanol, or the like; the ketone solvents may be acetone, methyl ethyl ketone, or the like; the ester solvents may be ethyl acetate, butyl acetate, or the like; the ether solvents may be tetrahydrofuran, diethyl ether, cyclopentyl methyl ether, or the like; and the nitrogen-containing solvents may be acetonitrile, nitromethane, N-methylpyrrolidone, or the like. Among these, the alcohol solvents are particularly preferred.

The amount of the solvent to be used is not particularly limited as long as the raw materials including the compounds of formulae (2) and (3) may be dissolved, and may be a suitable amount for the preparation of the present derivative, also taking other conditions, such as reaction temperature, into consideration.

The catalyst for the reaction of the compounds of formulae (2) and (3) may be an organic base or an inorganic base. In particular, in view of reactivity and solubility in the solvent, the catalyst is preferably an amine compound. Specifically, the catalyst may be a primary amine, such as methyl amine, a secondary amine, such as diisopropyl amine, or a tertiary amine, such as tryethyl amine, with secondary and tertiary amines being preferred. The amount of the catalyst is preferably 5 to 20 mol % with respect to 100 mol % of the compound of formula (2) or a salt thereof. At less than 5 mol %, the reaction rate may drastically be lowered, whereas at over 20 mol %, the ester portion of the compound of formula (3) (MPC) may be decomposed.

The reaction temperature in the reaction of the compounds of formulae (2) and (3) is preferably 10 to 60° C. At lower than 10° C., the reaction rate may drastically be lowered, whereas at over 60° C., side reactions may occur, such as ester decomposition reaction of MPC, or Michael addition reaction of the amino group of the compound of formula (2) to the double bond, resulting in lowering of the production yield of the present derivative.

The reaction time of the reaction of the compounds of the formulae (2) and (3) is preferably 6 to 96 hours, though depending on the catalyst and the reaction temperature. In a reaction time of less than 6 hours, the reaction may not reach the end point, whereas in a reaction time of over 96 hours, the present derivative, which is the reaction product, may be oxidized and deteriorated.

In the reaction of the compounds of formulae (2) and (3), it is preferred that the interior of the reaction vessel is replaced with an inert gas atmosphere, such as nitrogen or argon, for preventing a by-product disulfide compound.

Next, the protein adsorption inhibitor according to the present invention will be discussed. The protein adsorption inhibitor of the present invention contains the present derivative as an active component. The content of the present derivative in the protein adsorption inhibitor of the present invention is preferably 50 to 100 mass % for expression of effective protein adsorption inhibitory effect. The protein adsorption inhibitor of the present invention may also contain substances other than the present derivative, for example, reagents usually used in this art. Further, the protein adsorption inhibitor of the present invention may contain two or more derivatives of the present invention. In this case, it is preferred to adjust the total amount of the two or more derivatives within the above-mentioned range.

The protein adsorption inhibitor of the present invention, which contains 50 to 100 mass % of the present derivative as the active component, may be used in the applications to be discussed below to produce excellent effects.

The present derivative may be used in, other than the protein adsorption inhibitor, surface treatment of various medical instrument substrates, such as contact lenses, catheters, and guidewires, or surface treatment of physical and chemical instruments, such as microflow channels.

The protein adsorption inhibitor of the present invention may be used particularly in immunological determination using enzymatic reaction or antigen-antibody reaction with various antigens, antibodies, receptors, enzymes, or the like, in the presence of proteins, polypeptides, steroids, lipids, hormones, or the like. More specifically, the present inhibitor may be applied to known radioimmunoassay (RIA), enzyme immunoassay (EIA), fluoroimmunoassay (FIA), latex turbidimetry, western blotting, or the like. In such immunological determination, for example, an antibody or an antigen is bound to a substrate surface, such as an immune reaction vessel, and then the substrate surface portion to which the antibody or antigen is not bound is treated with the protein adsorption inhibitor of the present invention, so that the present derivative is firmly adsorbed to the substrate surface to inhibit adsorption of protein.

Next, the protein adsorption inhibitor solution of the present invention will be discussed. The protein adsorption inhibitor solution according to the present invention is a solution wherein 0.01 to 20 mass % of the present derivative is dissolved in a solvent. The concentration of the present derivative in the protein adsorption inhibitor solution of the present invention is 0.1 mass % or higher, more preferably 1.0 mass % or higher, and preferably 10 mass % or lower, more preferably 5.0 mass % or lower. At the concentration within these ranges, treatment of the substrate surface with the protein adsorption inhibitor solution of the present invention results in effective adsorption of the present derivative over the substrate surface, to thereby impart good protein adsorption inhibitory effect to the substrate. The protein adsorption inhibitor solution of the present invention may contain two or more derivatives of the present invention. In this case, it is preferred to adjust the total concentration of the two or more derivatives of the present invention within the above-mentioned ranges.

The protein adsorption inhibitor solution of the present invention may be obtained by dissolving the derivative of the present invention or the protein adsorption inhibitor of the present invention in a solvent or a buffer. The solvent may be purified water, pure water, ion-exchanged water, or alcohols, such as methanol, ethanol, 2-propanol, or organic solvents. The solvent is preferably water or ethanol, more preferably water. The buffer may be any buffer that may be used in immunological determination, such as phosphate buffer, acetate buffer, carbonate buffer, citrate buffer, Tris buffer, HEPES buffer, or physiological saline.

The protein adsorption inhibitor solution of the present invention may contain, in addition to the present derivative, compounds, such as reagents usually used in this art, for the purpose of improved reactivity or solution stability. Examples of such compounds may include amino acids, such as glycine, alanine, serine, threonine, glutamic acid, aspartic acid, glutamine, asparagine, lysine, or histidine, or amino-acid salts; peptides, such as glycylglycine; inorganic salts, such as phosphate, borate, sulfate, or Tris salt; and organic acids, such as flavins, acetic acid, citric acid, malic acid, maleic acid, or gluconic acid, or salts of organic acids.

The content of these compounds other than the present derivative in the protein adsorption inhibitor solution of the present invention may suitably be selected in view of the intended use of the solution, as far as the protein adsorption inhibitory effect derived from the present derivative is not inhibited.

Next, the phosphorylcholine-modified substrate having the present derivative adsorbed on a substrate surface is discussed. The substrate used in the present invention may be made of any material without particular limitation and may be, for example, polystyrene, polyvinyl chloride, polypropylene, acrylic resins, polymethylmethacrylate, glass, metal, ceramics, silicon rubber, polyvinylidene fluoride (abbreviated as PVDF hereinbelow), polyurethane, nylon, nitrocellulose, protein, polypeptides, or polysaccharides. Among these, polystyrene and PVDF are preferred, and polystyrene is particularly preferred.

The present derivative is also useful in inhibiting protein adsorption to magnetic microparticles. This means that the substrate of the phosphorylcholine-modified substrate of the present invention may be magnetic microparticles. The magnetic microparticles may be of any kind as long as a material that may be magnetized by magnetic induction is contained. Examples of such a material may include metals, such as ferrosoferric oxide ($Fe_3O_4$), iron sesquioxide ($\gamma$-$Fe_2O_3$), various ferrites, iron, manganese, or nickel, and alloys of cobalt, nickel, and/or manganese. In view of more efficient expression of the effect of the present invention, the magnetic microparticles are particles preferably having on their surface a polymer (resin) layer, a polar group, or a ligand, and preferably stable and insoluble in an aqueous medium. Magnetic microparticles having a polar group are not particularly limited, and may more preferably be magnetic microparticles having at least one polar group selected from the group consisting of an amino group, an aldehyde group, a carboxyl group, a tosyl group, a mercapto group, and an epoxy group.

The shape of the substrate is not particularly limited, and may specifically be, for example, in the form of membrane (film), plate, particles, porous body, gel, or a test tube, a vial container, a tube, or a flask.

The mechanism of adsorption of the present derivative to a substrate to form an adsorbed layer may be explained as follows. The present derivative may chemically react with reactive functional groups on the surface of the substrate to be adsorbed to the surface and form an adsorbed layer. Specifically, the present derivative may be adsorbed to the substrate surface through the reaction and binding between the amino group of the present derivative and a reactive functional group on the substrate surface, such as a carboxyl, epoxy, vinyl, or isocyanate group. Thus, presence of such a functional group on the substrate surface is preferred.

In the absence of such a functional group on the substrate surface, for example, when only functional groups that are non-reactive to an amino group, such as an amino group or a hydroxyl group, are present on the substrate surface, a functional group that is reactive to an amino group may be introduced to the substrate surface by means of a polyfunctional reagent, such as diisocyanate or dicarboxylic acid. The manner of introduction of such a reactive functional group to the substrate surface is not particularly limited, and may suitably be selected from known conditions, depending on the kind of substrate, its surface property, and the desired amount of the reactive functional group to be introduced.

Further, when the substrate surface has only hydrophobic groups, the present derivative may be reacted in advance with albumin or a hydrophobic compound, and then added in a solution or dispersion form to have the present derivative physically adsorbed to the substrate surface.

An example of a specific operation procedure for forming an adsorbed layer of the present derivative on a substrate surface having a functional group capable of binding with the present derivative, may be as follows. That is, a substrate is immersed in the protein adsorption inhibitor solution of the present invention, then thoroughly dried at a room temperature or by heating, to thereby form an adsorbed layer of the pre sent derivative adsorbed by binding to the substrate surface.

Next, an embodiment will be discussed of a method for inhibiting protein adsorption to a substrate, such as an immune reaction vessel, using the protein adsorption inhibitor solution of the present invention containing the present derivative. A substrate is immersed in the protein adsorption inhibitor solution of the present invention to react the present derivative with the surface of the substrate to bind to the surface, to thereby form an adsorbed layer of the derivative. A preferred immersion temperature is 4 to 37° C., and a preferred immersion time is 12 hours or more at 4° C., 1 to 12 hours at higher than 4° C. and lower than 25° C., and 0.5 to 2 hours at 25 to 37° C. The substrate used in the method for inhibiting protein adsorption of the present invention may be, for example, those mentioned for the substrate in the phosphorylcholine-modified substrate.

After the immersion is completed, the substrate is taken out of the protein adsorption inhibitor solution of the present invention, thoroughly dried at a room temperature or by heating, to thereby prepare a phosphorylcholine-modified substrate having an adsorbed layer of the present derivative formed. By using the phosphorylcholine-modified substrate in a measurement utilizing immune response, non-specific adsorption of antibodies or antigens, or protein in the specimen is inhibited. Before the drying, the substrate may be washed with water. The washing water may be ion-exchanged water, purified water, pure water, or the like. The drying at a room temperature or by heating is not essential, and the objective measurement may be performed without the drying step.

As an example of the method for inhibiting protein adsorption to a substrate by means of the protein adsorption inhibitor solution of the present invention, the immersion method is discussed above, but as long as the protein adsorption inhibitor solution is brought into contact with the substrate surface, any method may be employed. For example, when the substrate is a vessel or the like, the vessel may be filled with the protein adsorption inhibitor solution.

An embodiment of the method for inhibiting protein adsorption of the present invention is, as discussed above, to form an adsorbed layer of the present derivative on a substrate to inhibit adsorption of protein to the substrate in various measurements. That is, the present derivative inhibits access of protein or the like to the substrate surface to inhibit adsorption thereof, by coating, as an adsorbed layer, the substrate surface, such as an immune reaction vessel or measuring instrument.

Another embodiment of the method for inhibiting protein adsorption of the present invention is to add the protein adsorption inhibitor of the present invention to a reagent used in various determinations, such as immune response. That is, protein adsorption to the substrate is inhibited by forming an adsorbed layer of the present derivative on the substrate surface in one of the steps of various determinations. In this method, the protein adsorption inhibitor of the present invention may be added to any of the reagents and solutions used, except for the sample to be determined. In the present embodiment, the concentration of the present derivative in the reagent or solution to which the inhibitor of the present invention is added, is preferably 0.0125 to 5.0 mass %, more preferably 0.1 to 1.0 mass %, with respect to the total amount of the reagent or solution. In the present embodiment, it is, of course, necessary to bring the reagent or solution into contact with the substrate, before a protein-containing sample to be determined, such as serum, labeled antibodies, or labeled antigens, contacts the substrate.

In still another embodiment, the protein to be determined, such as an enzyme, labeled antibody, or labeled antigen, contained in a sample is first bound to the surface of the substrate, such as the above-mentioned immune reaction vessel or measurement instrument, and then the substrate may be treated with the protein adsorption inhibitor of the present invention. For example, when a polystyrene plate is used, protein to be determined is physically adsorbed or chemically bound to the plate, washed with a suitable solvent, and then the protein adsorption inhibitor solution of the present invention is brought into contact. In other words, the object to be determined is adsorbed to the plate surface, and then the present derivative is adsorbed to inhibit adsorption of the protein to the plate surface portion where the object is not adsorbed. In this way, the method inhibits non-specific adsorption of the protein to the substrate in the subsequent measurement procedure.

EXAMPLES

The present invention will now be explained in more detail based on Examples, but the present invention is not limited to these. In the following Examples, the compound of formula (1) will be simply referred to as the derivative.

Synthesis Example 1: Synthesis of Derivative 1 (m=3, n=44)

In a three-necked flask equipped with a thermometer, 2.16 g (7.31 mmol) of MPC was placed, 34.32 g of methanol was added and stirred homogeneously, and bubbled with nitrogen for 30 minutes. Then, 15.00 g (7.31 mmol) of α-aminopropyl-ω-mercaptoethoxy-polyoxyethylene hydrochloride (SUNBRIGHT SH-020PA (m=3, n=44), manufactured by NOF CORPORATION) and 0.077 mL (0.58 mmol) of diisopropylamine were added and stirred at 25° C. for 48 hours. The obtained reaction liquid was added dropwise to a cooled ethyl acetate, and the precipitate was filtered to obtain a white solid.

The obtained white solid was subjected to $^1$H-NMR analysis and IR analysis and the results are show below. IR was performed in FT/IR-6100 (JASCO CORPORATION), and NMR was performed in JNM-AL400 (JEOL LTD.).

<Results of IR and $^1$H-NMR Determinations of White Solid Obtained in Synthesis Example 1>

[IR]
3430 cm$^{-1}$ (—NH$_2$), 2875 cm$^{-1}$ (—CH), 1639 cm$^{-1}$ (C=O), 1457 cm$^{-1}$ (—CH), 1249 cm$^{-1}$ (P=O), 1102 cm$^{-1}$ (—OPOCH$_2$—), 953 cm$^{-1}$ (—Ni$^+$(CH$_3$)$_3$)

[$^1$H-NMR (D$_2$O Solvent)]
1.25 ppm (—CH$_3$), 1.94-1.99 ppm (H$_2$NCH$_2$CH$_2$CH$_2$O—), 2.77-2.89 ppm (—SCH$_2$CH(CH$_3$)—, H$_2$NCH$_2$CH$_2$CH$_2$O—), 3.10-3.14 ppm (NH$_2$CH$_2$CH$_2$CH$_2$O—), 3.22 ppm (—N$^+$(CH$_3$)$_3$), 2.66-3.74 ppm (—OCH$_2$CH$_2$S—), 3.84-3.90 ppm (—CH$_2$CH$_2$N+(CH$_3$)$_3$), 4.11-4.12 ppm (—CH$_2$CH$_2$N$^+$(CH$_3$)$_3$), 4.31-4.36 ppm (—OCH$_2$CH$_2$OP—)

Based on the results of the determinations, the obtained white solid was identified as Derivative 1 represented by formula (1-1) below.

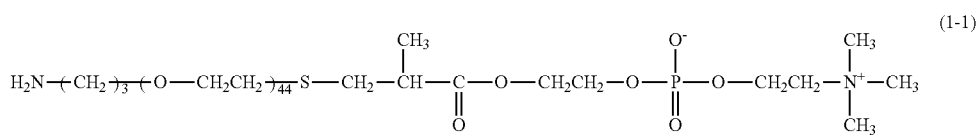

(1-1)

Comparative Synthesis Example 1: Synthesis of Copolymer 1 (MPC/BMA Copolymer)

In a mixed solvent of 30 g of ethanol and 30 g of distilled water, 17.85 g (60.45 mmol) of MPC and 2.15 g (15.12 mmol) of butyl methacrylate were dissolved, placed in a 500 mL four-necked flask equipped with a thermometer and a cooling tube, and bubbled with nitrogen for 30 minutes. Then, 0.328 g of azobisisobutyronitrile (AIBN) was added at 40° C. to polymerize for 4 hours, the temperature was raised to 70° C., and further reaction was effected for 3 hours, to thereby obtain a polymer. The polymer liquid was added dropwise into acetone and the precipitate was filtered, to thereby obtain Copolymer 1 in the form of a white solid.

The obtained Copolymer 1 was subjected to GPC analysis in HLC-8320GPC (TOSOH CORPORATION), and the molecular weight of Copolymer 1 was found to be 1210000 in terms of polyethylene glycol.

Example 1

<Preparation of Protein Adsorption Inhibitor Solution 1>

Protein Adsorption Inhibitor Solution 1 was prepared by dissolving Derivative 1 obtained in Synthesis Example 1 in a carbonate buffer (0.1 mol/L, pH 9.8) at a concentration of 1.0 mass %.

<Implementation of Method for Inhibiting Protein Adsorption to Substrate (Amino Plate), Preparation of Phosphorylcholine-Modified Substrate Having Derivative 1 Adsorbed to Substrate Surface, and Evaluation of Protein Adsorption Inhibitory Effect>

Immune reaction was determined in the following way, wherein the method for inhibiting protein adsorption to an amino plate was implemented to prepare a phosphorylcholine-modified substrate having Derivative 1 adsorbed on the substrate surface, and the protein adsorption inhibitory effect was evaluated.

To an amino plate (SUMITOMO BAKELITE CO., LTD.), 100 µL/well of 5 mM dimethyl suberimidate.2HCl (THERMOFISHER SCIENTIFIC K.K., referred to as DMS hereinbelow) solution (solvent: aqueous solution of 0.2 M triethanolamine) was added and left to stand at room temperature for 30 minutes. After the DMS solution was removed, 100 µL/well of Protein Adsorption Inhibitor Solution 1 was added, left to stand at room temperature for 1 hour, and then Protein Adsorption Inhibitor Solution 1 was removed. Then, 100 µL/well of HRP-labeled IgG (BIORAD LABORATORIES, INC.) diluted to 72000 folds with Dulbecco's phosphate buffered saline (—) (referred to as PBS hereinbelow) was added and left to stand at room temperature. The HRP-labeled IgG solution in the wells was removed, and washing by adding 200 mL/well of PBS containing 0.05% Tween 20 and removing was repeated four times. After the washing, 100 µL/well of a chromogenic solution for HRP (KPL) was added, and reacted at room temperature for 7 minutes. After the seven minutes, the reaction was terminated by adding 50 µL/well of 2N sulfuric acid, and the absorbance at 450 nm was measured in a microplate reader (MOLECULAR DEVICES, LLC) to thereby detect the protein adsorbed to the interior of the wells. The absorbance was determined as an average of three measurements. A smaller absorbance indicates more inhibited protein adsorption.

The protein adsorption inhibitory effect was evaluated with the relative protein adsorption ratio calculated by the following formula from the absorbance in Example 1 and the absorbance in the following Comparative Example 1. That is, the protein adsorption ratio to the amino plate in Example 1 was evaluated by a relative adsorption ratio with respect to the protein adsorption ratio to the amino plate in Comparative Example 1 being 100%. The results are shown in Table 1.

Protein adsorption ratio in Example 1=(Absorbance in Example 1/Absorbance in Comparative Example 1)×100

Comparative Example 1

Immune reaction was determined in the same way as in Example 1, except that Protein Adsorption Inhibitor Solution 1 was replaced with a carbonate buffer without Derivative 1 dissolved therein, and the absorbance was measured in the same way as in Example 1. The results are shown in Table 1. The protein adsorption ratio in Comparative Example 1 was taken as 100%.

TABLE 1

|  | Absorbance (450 nm) | Protein Adsorption Ratio (%) |
| --- | --- | --- |
| Example 1 | 0.448 | 46.3 |
| Comparative Example 1 | 0.968 | 100 |

As apparent from Table 1, in Example 1, wherein the method of the present invention for inhibiting protein adsorption to the substrate using Derivative 1 was implemented, the absorbance was half or less, and the protein adsorption ratio to the substrate amino plate was half or less, of the absorbance and the protein adsorption ratio, respectively, in Comparative Example 1, wherein the method for inhibiting protein adsorption was not implemented. Thus, it is demonstrated that the non-specific adsorption of protein to the amino plate was effectively inhibited.

Example 2

<Washability (Anti-Desorption Property)>

The washability of Derivative 1 obtained in Synthesis Example 1 was evaluated in comparison to Copolymer 1 in the following method. That is, the difference in absorbance between with and without washing of Derivative 1-modified substrate wherein the Derivative 1 was adsorbed to the substrate surface was compared to the difference in absorbance between with and without washing of Copolymer 1-modified substrate wherein the Copolymer 1 was adsorbed to the substrate surface, and the resistances to washing of Derivative 1 and Copolymer 1 were evaluated. Specifically, the washability was calculated from the absorbance with washing and the absorbance without washing by the following formula, and evaluated.

Washability (%)=(Absorbance without washing/Absorbance with washing)×100

With regard to the washability, a larger value, i.e., a smaller difference in absorbance between with and without washing, indicates less desorption by washing of the material adsorbed to the substrate (lower desorption ratio), and thus better washability.

Example 2-1

Using Protein Adsorption Inhibitor Solution 1, immune reaction was determined in the same way as in Example 1 and the absorbance was also measured in the same way.

Example 2-2

Immune reaction was determined in the same way as in Example 1 and the absorbance was also measured in the same way, except that after the removal of Protein Adsorption Inhibitor Solution 1, the washing by adding 200 µL/well of PBS and removing was repeated three times.

The washability was calculated from the absorbance in Example 2-1 and the absorbance in Example 2-2 by the above formula. The results are shown in Table 2.

Comparative Example 2-1

A PBS solution of Copolymer 1 was used, wherein 1.0 mass % of Copolymer 1 in place of Protein Adsorption Inhibitor Solution 1 was dissolved in PBS. Further, Nunc MaxiSoap plate (THERMOFISHER SCIENTIFIC K.K.)

was used and DMS was not added. Other than these, immune reaction was determined in the same way as in Example 1 and the absorbance was also measured in the same way.

Comparative Example 2-2

Immune reaction was determined in the same way as in Comparative Example 2-1 and the absorbance was also measured in the same way, except that after the removal of the PBS solution of Copolymer 1, the washing by adding 200 µL/well of PBS and removing was repeated three times.

The washability was calculated from the absorbance in Comparative Example 2-1 and the absorbance in Comparative Example 2-2 by the above formula. The results are shown in Table 2.

Comparative Example 2-3

Immune reaction was determined in the same way as in Example 1 and the absorbance was also measured in the same way, except that a PBS solution of Copolymer 1 was used, wherein 1.0 mass % of Copolymer 1 in place of Protein Adsorption Inhibitor Solution 1 was dissolved in PBS.

Comparative Example 2-4

Immune reaction was determined in the same way as in Comparative Example 2-3 and the absorbance was also measured in the same way, except that after the removal of the PBS solution of Copolymer 1, the washing by adding 200 µL/well of PBS and removing was repeated three times.

The washability was calculated from the absorbance in Comparative Example 2-3 and the absorbance of Comparative Example 2-4 by the above formula. The results are shown in Table 2.

TABLE 2

|  | Absorbance (450 nm) | Washability (%) |
| --- | --- | --- |
| Example 2-1 | 0.448 | 95.5 |
| Example 2-2 | 0.468 |  |
| Comparative Example 2-1 | 0.471 | 43.1 |
| Comparative Example 2-2 | 1.094 |  |
| Comparative Example 2-3 | 0.317 | 24.8 |
| Comparative Example 2-4 | 1.281 |  |

As apparent from Table 2, the desorption ratio of Derivative 1 from the substrate by washing was extremely low compared to the desorption ratio of Copolymer 1 by washing, which demonstrates that the washability is superior.

Example 3-1

Immune reaction was determined in the following way, wherein the method for inhibiting protein adsorption to magnetic microparticles was implemented to prepare Derivative 1-bound magnetic microparticles having Derivative 1 adsorbed on the particle surface, and the protein adsorption inhibitory effect was evaluated.
<Reaction to Magnetic Microparticles>
In a polypropylene microtube, 16 µL of magnetic microparticles (THERMOFISHER SCIENTIFIC K.K., Dynabeads (trademark) MyOne (trademark) carboxylic acid) was placed, and washing by adding 32 µL of MES/NaOH buffer (10 mM, pH 5.0, referred to as MES buffer hereinbelow) and removing was repeated twice. Then, 2 µL of a water-soluble carbodiimide solution (dissolved in the MES buffer at 20 mg/mL) and 2 µL of an N-hydroxysuccinimide solution (dissolved the MES buffer at 12 mg/mL) were added and reacted at room temperature for 30 minutes. After the reaction, washing by adding 32 µL of the MES buffer and removing was performed, and 8 µL of a solution of Derivative 1 of Synthesis Example 1 dissolved at 1 wt % in a 25 mM CAPS/NaOH buffer (pH 10.0, referred to as CAPS buffer hereinbelow), stirred, and reacted at 37° C. for 2 hours. This was recovered as Derivative 1-bound magnetic microparticles. Here, a neodymium magnet was used for washing and recovering of the magnetic microparticles.
<Protein Adsorption Test on Derivative 1-Bound Magnetic Microparticles>

To the Derivative 1-bound magnetic particles, 784 µL of HEPES buffer containing 0.05% Tween 20 (referred to as HEPES-T buffer hereinbelow) was added, stirred, and dispensed to a V-bottom 96 well plate by 100 µL/well, and the supernatant was discarded. To the plate, 100 µL/well of HRP-labeled IgG diluted to 10000 folds with the HEPES buffer was added, and left to stand at room temperature for 1 hour. Then, washing by adding 100 µL/well of the HEPES-T buffer and removing was repeated four times. After the washing, 100 µL/well of a chromogenic solution for HRP (KPL) was added, and reacted at room temperature for 7 minutes. After the seven minutes, the reaction was terminated by adding 50 µL/well of 2N sulfuric acid. The reaction liquid was transferred to a flat-bottom 96 well plate by 100 µL/well, and the absorbance at 450 nm was measured in a microplate reader (MOLECULAR DEVICES, LLC) to thereby detect the protein adsorbed to interior of the wells. The results are shown in Table 3. A smaller absorbance indicates more inhibited protein adsorption.

The protein adsorption inhibitory effect was evaluated with the relative protein adsorption ratio calculated by the following formula from the absorbance in Example 3-1 and the absorbance in the following Comparative Example 3-1. That is, the protein adsorption ratio to the magnetic microparticles in Example 3-1 was evaluated by a relative adsorption ratio with respect to the protein adsorption ratio to the magnetic microparticles in Comparative Example 3-1 being 100%. The results are shown in Table 3. Protein adsorption ratio in Example 3-1=(Absorbance in Example 3-1/Absorbance in Comparative Example 3-1)×100

Example 3-2

Immune reaction was determined in the same way as in Example 3-1, except that, after the reaction of Derivative 1 at 37° C. for 2 hours, washing by adding 16 µL of 50 mM HEPES/NaOH buffer (pH 7.4, referred to as HEPES buffer hereinbelow) and removing was repeated twice, and the protein adsorption ratio was calculated from the obtained absorbance. The results are shown in Table 3.

Example 3-3

Immune reaction was determined in the same way as in Example 3-1, except that the concentration of Derivative 1 was 4 wt %, and the protein adsorption ratio was calculated from the obtained absorbance. The results are shown in Table 3.

Comparative Example 3-1

Immune reaction was determined in the same way as in Example 3-1, except that a carbon buffer without Derivative 1 dissolved therein was used, and the protein adsorption ratio was calculated from the obtained absorbance. The results are shown in Table 3.

Comparative Example 3-2

Immune reaction was determined in the same way as in Example 3-1, except that Derivative 1 was replaced with Copolymer 1, and the protein adsorption ratio was calculated from the obtained absorbance. The results are shown in Table 3.

Comparative Example 3-3

Immune reaction was determined in the same way as in Example 3-2, except that Derivative 1 was replaced with Copolymer 1, and the protein adsorption ratio was calculated from the obtained absorbance. The results are shown in Table 3.

TABLE 3

|  | Absorbance (450 nm) | Adsorption Ratio (%) |
| --- | --- | --- |
| Example 3-1 | 0.113 | 4.0 |
| Example 3-2 | 0.128 | 4.5 |
| Example 3-3 | 0.070 | 2.5 |
| Comparative Example 3-1 | 2.835 | 100 |
| Comparative Example 3-2 | 0.31 | 10.9 |
| Comparative Example 3-3 | 0.63 | 22.2 |

As apparent from Table 3, when the magnetic microparticles are used as the substrate, the present derivative exhibits excellent protein adsorption inhibitory effect. Further, from the comparison of Examples 3-1 and 3-1 and Comparative Examples 3-2 and 3-3, it is demonstrated that the present derivative exhibits excellent washability even when the magnetic microparticles were used as the substrate.

What is claimed is:

1. A phosphorylcholine group-containing polyethylene glycol derivative represented by formula (1):

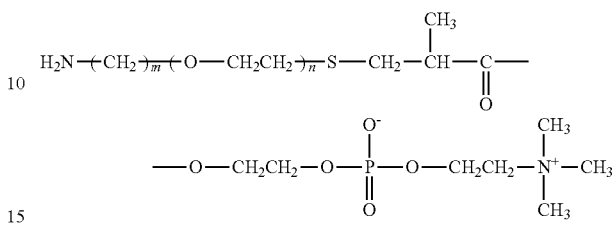

wherein m is an integer of 1 to 10 and n is an integer of 20 to 200.

2. A protein adsorption inhibitor comprising the phosphorylcholine group-containing polyethylene glycol derivative according to claim 1, as an active component.

3. A protein adsorption inhibitor solution comprising 0.01 to 20 mass % of the phosphorylcholine group-containing polyethylene glycol derivative according to claim 1.

4. A phosphorylcholine-modified substrate consisting of a substrate and the phosphorylcholine group-containing polyethylene glycol derivative according to claim 1, wherein said phosphorylcholine group-containing polyethylene glycol derivative is adsorbed on a surface of the substrate.

5. A method for inhibiting protein adsorption to a substrate, comprising forming an adsorbed layer of a phosphorylcholine group-containing polyethylene glycol derivative by treating a surface of a substrate with the protein adsorption inhibitor solution according to claim 3.

* * * * *